United States Patent
Kwak et al.

(10) Patent No.: US 10,758,746 B2
(45) Date of Patent: Sep. 1, 2020

(54) RADIOTHERAPY ASSISTANT APPARATUS FOR MODULATING BUILD-UP REGION OF PHOTON BEAM, RADIOTHERAPY SYSTEM AND METHOD THEREFOR

(71) Applicants: THE ASAN FOUNDATION, Seoul (KR); UNIVERSITY OF ULSAN FOUNDATION FOR INDUSTRY COOPERATION, Ulsan (KR)

(72) Inventors: Jung Won Kwak, Namyangju-si (KR); Sang Wook Lee, Seoul (KR); Byung Chul Cho, Anyang-si (KR); Seung Do Ahn, Seoul (KR); Won Sik Choi, Seoul (KR); Woo Sang Ahn, Gangneung-si (KR); Chi Young Jeong, Seoul (KR); Seong Soo Shin, Seoul (KR); Kyoung Jun Yoon, Seoul (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 130 days.

(21) Appl. No.: 16/015,974

(22) Filed: Jun. 22, 2018

(65) Prior Publication Data

US 2018/0369610 A1 Dec. 27, 2018

(30) Foreign Application Priority Data

Jun. 23, 2017 (KR) .................. 10-2017-0079502

(51) Int. Cl.
*A61N 5/10* (2006.01)
*A61B 6/00* (2006.01)

(52) U.S. Cl.
CPC ......... *A61N 5/1031* (2013.01); *A61N 5/1049* (2013.01); *A61N 5/1065* (2013.01);
(Continued)

(58) Field of Classification Search
CPC .. A61N 5/1031; A61N 5/1077; A61N 5/1065; A61N 5/1071; A61N 5/1049;
(Continued)

(56) References Cited

U.S. PATENT DOCUMENTS

2011/0012593 A1* 1/2011 Shvartsman ......... A61N 5/1039
324/307
2013/0035586 A1* 2/2013 Knox .................... A61N 5/1049
600/411

(Continued)

FOREIGN PATENT DOCUMENTS

JP H11-253563 A 9/1999
JP 2007-165250 A 6/2007

(Continued)

OTHER PUBLICATIONS

An Office Action mailed by the Korean Intellectual Property Office dated Jun. 21, 2018, which corresponds to Korean Patent Application No. 10-2017-0079502 and is related to U.S. Appl. No. 16/015,974; with English translation.

(Continued)

*Primary Examiner* — Christine S. Kim
(74) *Attorney, Agent, or Firm* — Studebaker & Brackett PC

(57) ABSTRACT

Disclosed are a radiotherapy assistant apparatus for modulating a build-up region of a photon beam for a radiotherapy, a radiotherapy system including the radiotherapy assistant apparatus, and method for the radiotherapy system. The radiotherapy assistant apparatus for modulating a build-up region of a photon beam for a radiotherapy, including at least: a magnetic field generator that generates a magnetic field that has a direction perpendicular to a movement direction of the photon beam, the magnetic field generator is disposed on a movement route along which the photon beam moves toward a target portion of the radiotherapy; and a (Continued)

magnetic field intensity adjuster that adjusts an intensity of the magnetic field generated by the magnetic field generator. The magnetic field generator disperses secondary electrons that have particular energy levels equal to or lower than a preset value.

20 Claims, 7 Drawing Sheets

(52) U.S. Cl.
CPC ......... *A61N 5/1071* (2013.01); *A61N 5/1077* (2013.01); *A61B 6/4241* (2013.01); *A61N 5/1069* (2013.01); *A61N 2005/1061* (2013.01); *A61N 2005/1072* (2013.01); *A61N 2005/1091* (2013.01); *A61N 2005/1095* (2013.01)

(58) Field of Classification Search
CPC .......... A61N 2005/1095; A61N 5/1069; A61N 2005/1072; A61N 2005/1061; A61N 2005/1091; A61N 2005/1089; A61N 2005/1096; A61N 2005/1094; A61N 5/1028; A61B 6/4241
See application file for complete search history.

(56) References Cited

U.S. PATENT DOCUMENTS

| 2014/0021358 | A1* | 1/2014 | Wieringa | G01T 1/1603 |
| | | | | 250/366 |
| 2017/0080253 | A1* | 3/2017 | Clayton | A61N 5/1067 |
| 2019/0118000 | A1* | 4/2019 | Kwak | A61N 5/1065 |

FOREIGN PATENT DOCUMENTS

| JP | 2007-525249 A | 9/2007 |
| KR | 10-1378447 B1 | 3/2014 |
| KR | 10-2016-0076703 A | 7/2016 |

OTHER PUBLICATIONS

Woo Sang Ahn; "Usefulness Evaluation for Modulation Technique Using Magnetic Field, for Build-up Region of 6MV Photon Beam"; The Korean Magnetics Society and Winter Conference; Nov. 25, 2016.

Seong Soo Shin et al.; "Effect of Transverse Magnetic Field on Build-up Region of 6MV Photon Beam"; Journal of the Korean Magnetics Society; Feb. 2017; pp. 18-22; vol. 27, No. 1.

* cited by examiner (a) Open beam  (b) Magnetic field of 0.5 T

RADIOTHERAPY ASSISTANT APPARATUS FOR MODULATING BUILD-UP REGION OF PHOTON BEAM, RADIOTHERAPY SYSTEM AND METHOD THEREFOR

CROSS-REFERENCE TO RELATED APPLICATIONS

A claim for priority under 35 U.S.C. § 119 is made to Korean Patent Application No. 10-2017-0079502 filed Jun. 23, 2017 in the Korean Intellectual Property Office, the entire contents of which are hereby incorporated by reference.

BACKGROUND

Embodiments of the inventive concept described herein relate to an apparatus for modulating build-up regions of photon beams by using a magnetic field and a beam spoiler, a radiotherapy apparatus based on photon beams including the same, and a method for modulating build-up regions of a photon beam by using a magnetic field and a beam spoiler, and more particularly, to an apparatus for modulating build-up regions, by which a depth dose is modulated in build-up regions of photon beams, a radiotherapy apparatus including the same, and a method for modulating build-up regions of photon beams.

A radiotherapy apparatus is a medical instrument that uses radioactive rays in treatment of diseases, and is widely used to delay, stop, or destruct growth of a malicious tumor tissue such as a cancer by using X-rays, photons, and charged radioactive rays, such as electron beams.

Meanwhile, when an excessive amount of radioactive rays having high energy are delivered to normal tissues or organs of a human body, DNA molecules are ionized and damaged, causing a mutation or killing cells so that the mutation caused due to the DNA damage may cause a genetic defect and may cause a cancer. Accordingly, when normal tissues and a tumor are close to each other, the radiotherapy dose often is not sufficiently irradiated due to a side-effect of the radioactive rays.

Accordingly, during the radiotherapy, the amount of radioactive rays and the disposition of the radioactive rays have to be adjusted such that a tumor that is to be destructed receives a sufficient amount of radioactive rays and a damage to normal tissues that surrounds the tumor is minimized.

SUMMARY

When radiotherapy is performed on a tumor (for example, a Glottic cancer) located in a specific depth from a surface (for example, skin or a mucous membrane) of a portion of a human body, a high dose is provided to a normal tissue on a route for approach to the tumor to provide a desired dose to the tumor by using a photon beam (that is, a linear accelerator).

In detail, a sufficient build-up of a dose is made by attaching a bolus that is a tissue equivalent material to skin such that it looks as if a tumor that is a target portion was located in a deep location from the surface by a thickness of the tissue equivalent material. However, the scheme of attaching a tissue equivalent material provides a build-up effect to the target radiotherapy point, but a normal tissue located on the movement route of radioactive rays is exposed to a high dose.

Accordingly, Embodiment of the inventive concept provide an apparatus for modulating build-up regions of a photon beam by using a magnetic field and a beam spoiler by which a damage of a normal tissue (particularly, a surface area of skin) may be prevented by reducing an amount of radioactive rays that are provided to a normal tissue located before a target radiotherapy point in a radiotherapy process, a radiotherapy apparatus based on a photon beam including the same, and a method for modulating build-up regions of a photon beam by using a magnetic field and a beam spoiler according to embodiments of the inventive concept will be described in detail.

Embodiments of the inventive concept also provide an apparatus for modulating build-up regions of a photon beam by using a magnetic field and a beam spoiler by which dose effect of a build-up region may be provided to a target radiotherapy point (that is, a tumor located in a specific depth from a surface of a human body) and a effect of dose reduction may be provided to normal tissues located before a target radiotherapy point, a radiotherapy apparatus based on a photon beam including the same, and a method for modulating build-up regions of a photon beam by using a magnetic field and a beam spoiler according to embodiments of the inventive concept will be described in detail. That is, embodiments of the inventive concept provides an apparatus and a method for reducing a dose in a surface area of skin while increasing a dose of a tumor located around an epidermis of skin to reduce a side-effect of radioactive rays, by modulating a depth dose in a build-up region by a photon beam provided through the surface of the skin.

The technical objects of the inventive concept are not limited to the above-mentioned ones, and the other unmentioned technical objects will become apparent to those skilled in the art from the following description.

In accordance with an aspect of the inventive concept, there is provided a radiotherapy assistant apparatus for modulating a build-up region of a photon beam for a radiotherapy, including a magnetic field generator that generates a magnetic field that has a direction perpendicular to a movement direction of the photon beam, the magnetic field generator is disposed on a movement route along which the photon beam moves toward a target portion of the radiotherapy, and a magnetic field intensity adjuster that adjusts an intensity of the magnetic field generated by the magnetic field generator, wherein the magnetic field generator disperses secondary electrons that have particular energy levels equal to or lower than a preset value.

In accordance with another aspect of the inventive concept, there is provided an radiotherapy assistant apparatus for modulating a build-up region of a photon beam for a radiotherapy, including a magnetic field generator that generates a magnetic field that has a direction perpendicular to a movement direction of the photon beam, the magnetic field generator is disposed on a movement route along which the photon beam moves toward a target portion of the radiotherapy, and a beam spoiler disposed on the movement route, the beam spoiler generates, when the photon beam passes through the beam spoiler, secondary electrons, wherein the magnetic field generator disperses secondary electrons having particular energy levels equal to or lower than a preset value, among the secondary electrons generated by the beam spoiler and secondary electrons included in the photon beam.

In accordance with another aspect of the inventive concept, there is provided a radiotherapy method for modulating a build-up region of a photon beam for a radiotherapy, including generating, by a linear accelerator of a radiotherapy apparatus, the photon beam, generating, by a beam spoiler of a radiotherapy assistant apparatus, secondary electrons when the generated photon beam passes through the beam spoiler, generating, by a magnetic field generator of the radiotherapy assistant apparatus, a magnetic field that has a direction perpendicular to a movement direction of the photon beam, and dispersing, by the magnetic field generator of the radiotherapy assistant apparatus, secondary electrons having particular energy levels equal to or lower than a preset value, among the secondary electrons generated by the beam spoiler and secondary electrons included in the photon beam, wherein an intensity of the magnetic field generated by the magnetic field generator is adjusted by a magnetic field intensity adjuster of the radiotherapy assistant apparatus, based on a radiotherapy condition.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
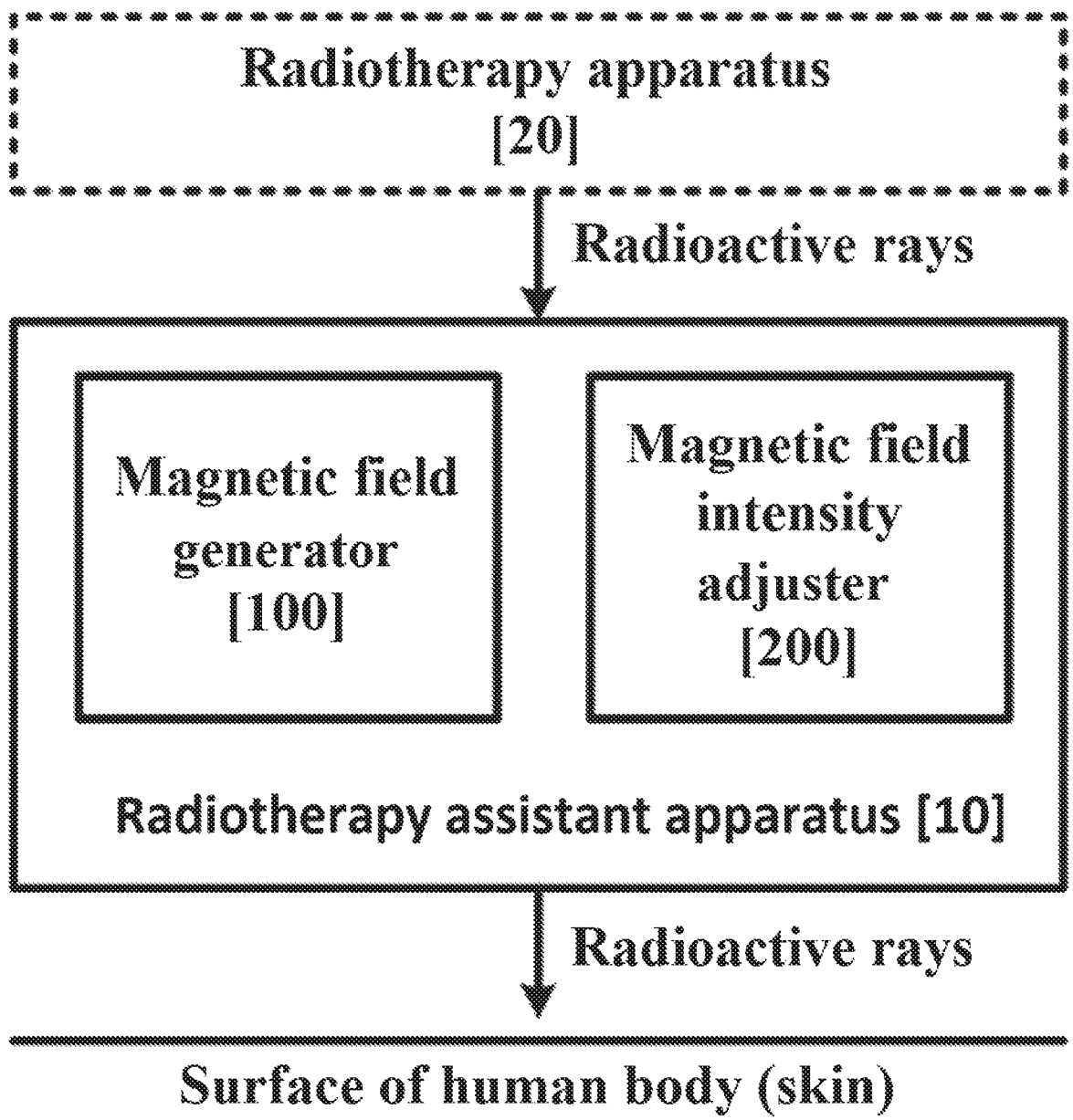
FIG. 1 is a diagram of a radiotherapy system according to an embodiment of the inventive concept.

Hereinafter, exemplary embodiments of the inventive concept will be described in detail with reference to the accompanying drawings. The above and other aspects, features and advantages of the invention will become apparent from the following description of the following embodiments given in conjunction with the accompanying drawings. However, the inventive concept is not limited to the embodiments disclosed below, but may be implemented in various forms. The embodiments of the inventive concept are provided to make the disclosure of the inventive concept complete and fully inform those skilled in the art to which the inventive concept pertains of the scope of the inventive concept. The same reference numerals denote the same elements throughout the specification.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other elements, in addition to the aforementioned elements.

Hereinafter, an apparatus for modulating build-up regions of a photon beam by using a magnetic field and a beam spoiler, a radiotherapy apparatus based on a photon beam including the same, and a method for modulating build-up regions of a photon beam by using a magnetic field and a beam spoiler according to embodiments of the inventive concept will be described in detail.

When radiotherapy is performed on a tumor (for example, a Glottic cancer) located in a specific depth from a surface (for example, skin or a mucous membrane) of a portion of a human body, a high dose is provided to normal tissues on a route for approach to the tumor to provide a desired dose to the tumor by using a photon beam generator (that is, a linear accelerator).

Figure 3:
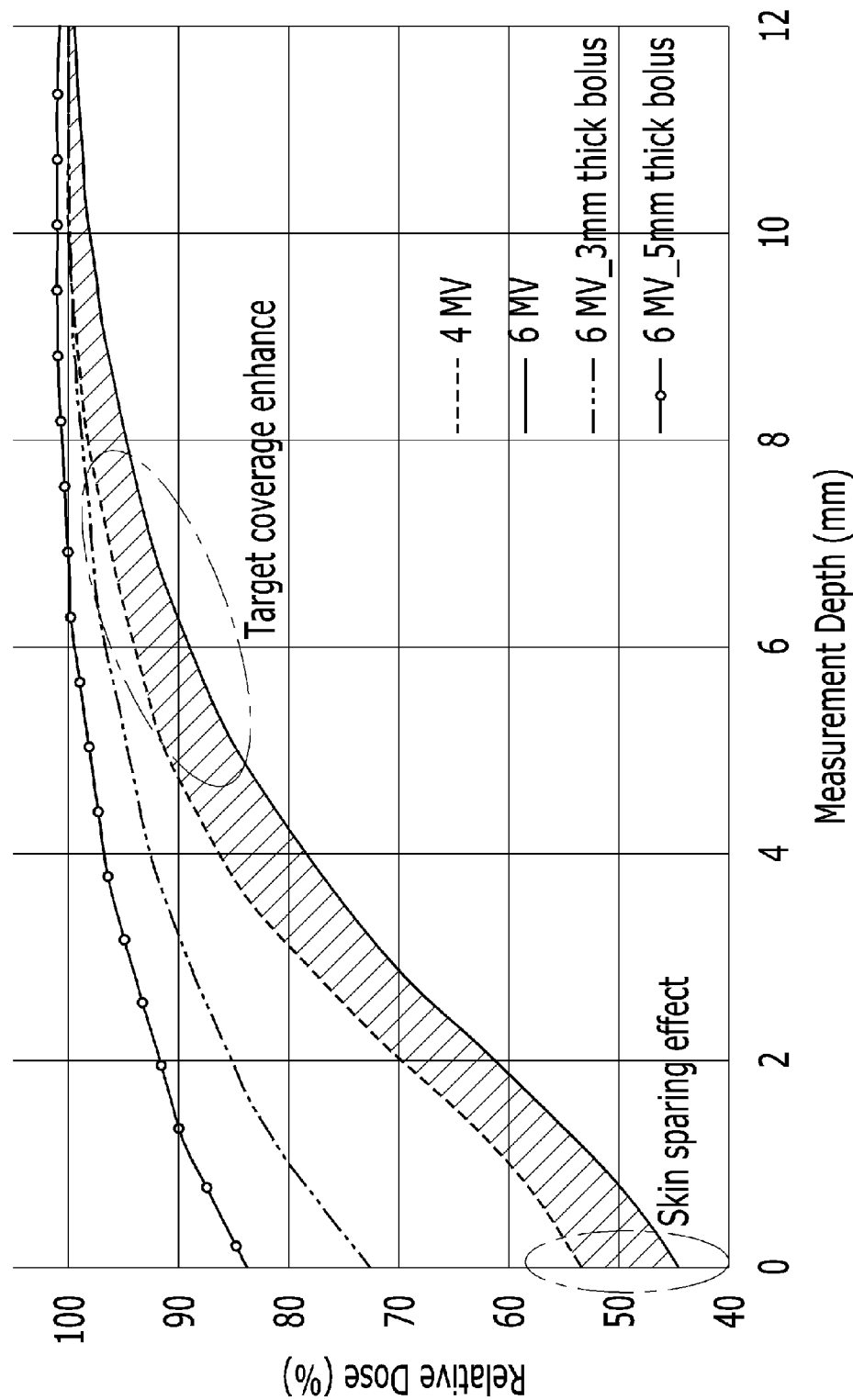
FIG. 3 is a graph depicting changes of build-up regions for depths from a surface of skin of the case in which a photon beam is provided in a general condition (an open beam condition) and the case in which a photon beam is provided after a tissue equivalent material is attached to skin.

Conventionally, a sufficient build-up of a dose is made by attaching a bolus that is a tissue equivalent material to skin such that it looks as if a tumor that is a target portion was located in a deep location from the surface of the skin by a thickness of the tissue equivalent material. However, although a build-up of a dose is made at a target radiotherapy point in the scheme of attaching the tissue equivalent material to the surface of the skin, a normal tissue (particularly, the surface of the skin) located in a movement route of the radioactive ray as in FIG. 3.

That is, it has been considered that a build-up of a dose at a target portion and a dose reduction in the normal tissue (particularly, a surface of skin) before the target radiotherapy portion are in a trade-off relationship. Accordingly, the inventive concept provides an apparatus for modulating build-up regions of a photon beam by using a magnetic field and a beam spoiler by which a build-up of a dose at a target portion and a dose reduction of a normal tissue (particularly, a surface of skin) before the target radiotherapy portion may be made at the same time, a radiotherapy apparatus based on a photon beam including the same, and a method for modulating a build-up region of a photon beam by using a magnetic field and a beam spoiler according to embodiments of the inventive concept will be described in detail.

FIG. 1 is a diagram of a radiotherapy system including a radiotherapy assistant apparatus 10 for modulating a build-up region according to an embodiment of the inventive concept.

Figure 2:
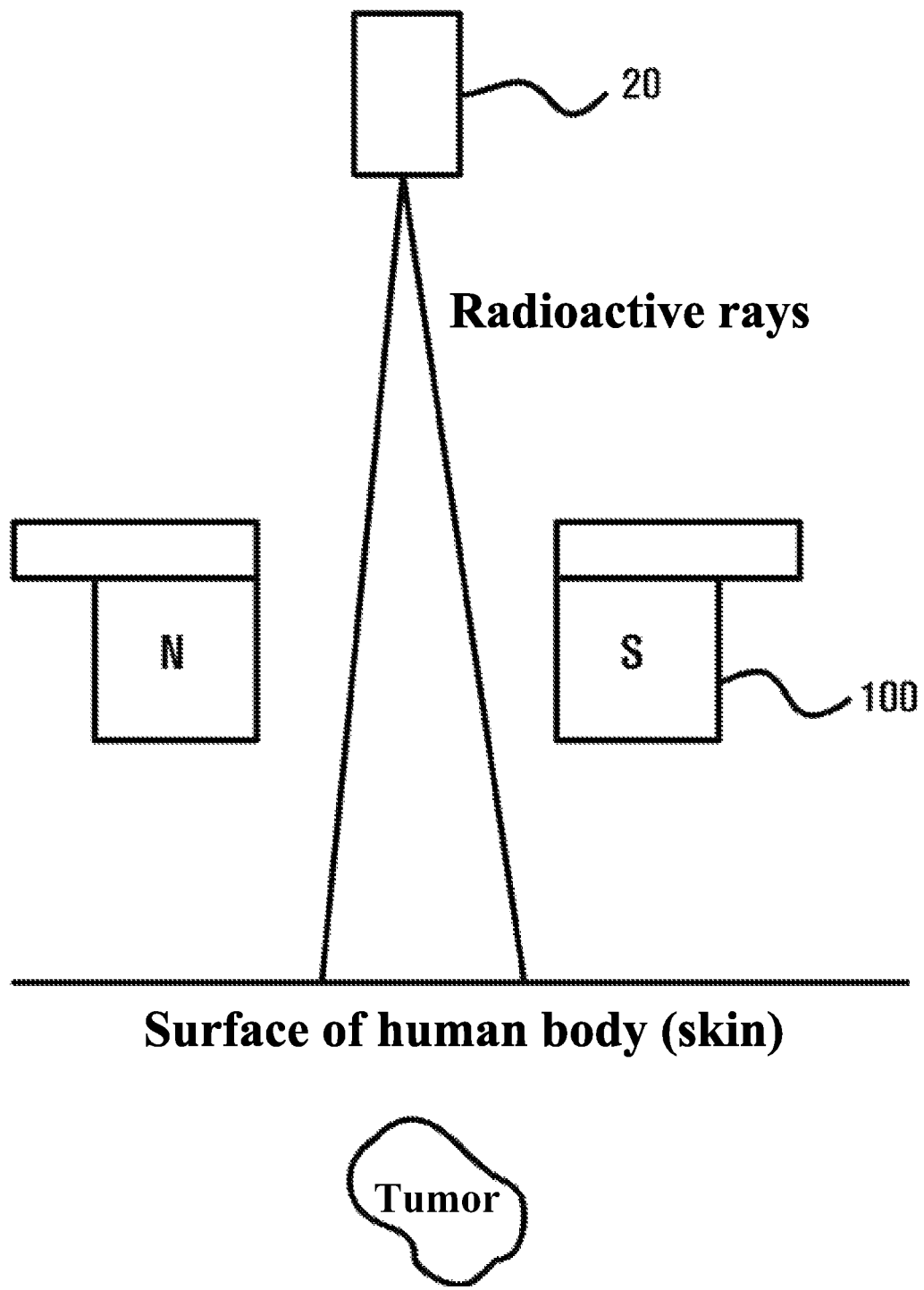
FIG. 2 is an exemplary view of a radiotherapy system according to the embodiment of the inventive concept performs radiotherapy.

FIG. 2 is an exemplary view that is applied the radiotherapy system for modulating a build-up region according to the embodiment of the inventive concept performs radiotherapy.

Referring to FIGS. 1 and 2, the apparatus 10 for modulating a build-up region according to the embodiment of the inventive concept includes a magnetic field generator 100, and a magnetic field intensity adjuster 200.

The magnetic field generator 100 functions to disperse secondary electrons of a specific energy level or less by forming a magnetic field area on a movement route of a radioactive ray. In an embodiment, the magnetic field generator 100 includes a pair of electromagnets or permanent magnets that are disposed on opposite sides while having opposite polarities. That is, the magnetic field generator 100 functions to apply a magnetic field in a direction that is perpendicular to the movement direction of the radioactive ray.

It is preferable that a radiotherapy apparatus 20 (or a radioactive ray generator) that uses the apparatus 10 for modulating a build-up region be a linear accelerator (LINAC) that generates a range of MV energies X-rays. The radiotherapy apparatus 20 delivers kinetic energy to secondary electrons through a reaction due to Compton effect on a surface of a material that is exposed to radiation due to the characteristics of X-ray beams in a generated MV area, and delivers the radioactive dose to the interior of the human body by using electrons.

Figure 4:
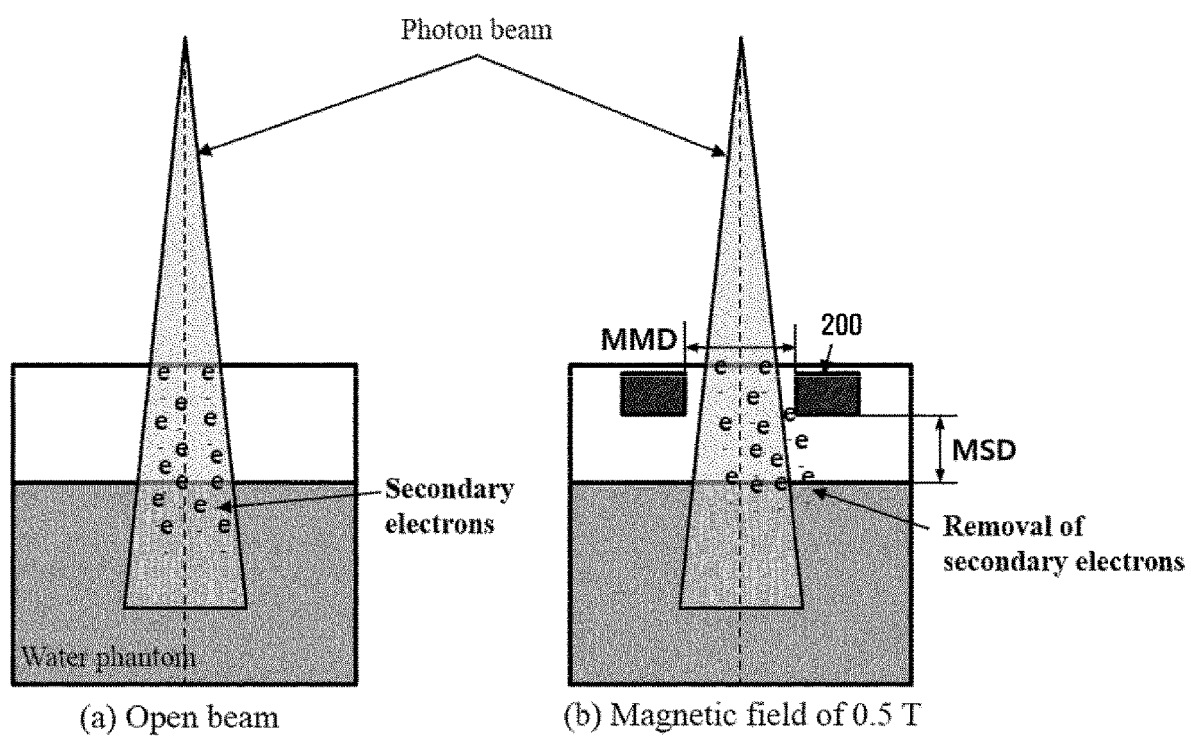
FIG. 4 is an exemplary view comparing movement routes of low-energy secondary electrons of case (a) in which a radioactive ray is provided while a magnetic field is not applied and case (b) in which a radioactive ray is provided while a magnetic field is applied.

The magnetic field generator 100 is disposed on the outside of the human body on a route along which a photon beam is incident to a target portion (or a target portion). The magnetic field generator 100 generates a magnetic field in a direction that is perpendicular to the movement direction of the secondary electrons on the outside of the human body before the secondary electrons enter the interior of the human body, and as in FIG. 4, the secondary electrons are biased or dispersed by a force of a magnetic field, for example, a Lorentz's force while passing through the magnetic field area formed by the magnetic field generator 100. The magnetic field intensity adjuster 200 functions to adjust the intensity of a magnetic field of the magnetic field generator 100. Because the biasing degree of the secondary electrons varies according to the intensity of a magnetic field, the magnetic field intensity adjuster 200 provides a function that prevents secondary electrons of low energy from contributing to skin dose. For example, because secondary electrons having low kinetic energy reaches a tumor tissue to provide a radiotherapy effect when the target radiotherapy portion is located at a point that is close to the surface of skin as compared with the case in which the target radiotherapy portion is located at a deep point from a surface of skin, a reference for a level of kinetic energy of secondary electrons that is biased not to proceed towards the target radiotherapy portion may be set to be low by applying a magnetic field of a low intensity to the magnetic field generator 100. The main feature is to provide only secondary electrons with energy that can just affect the build-up region.

Figure 5:
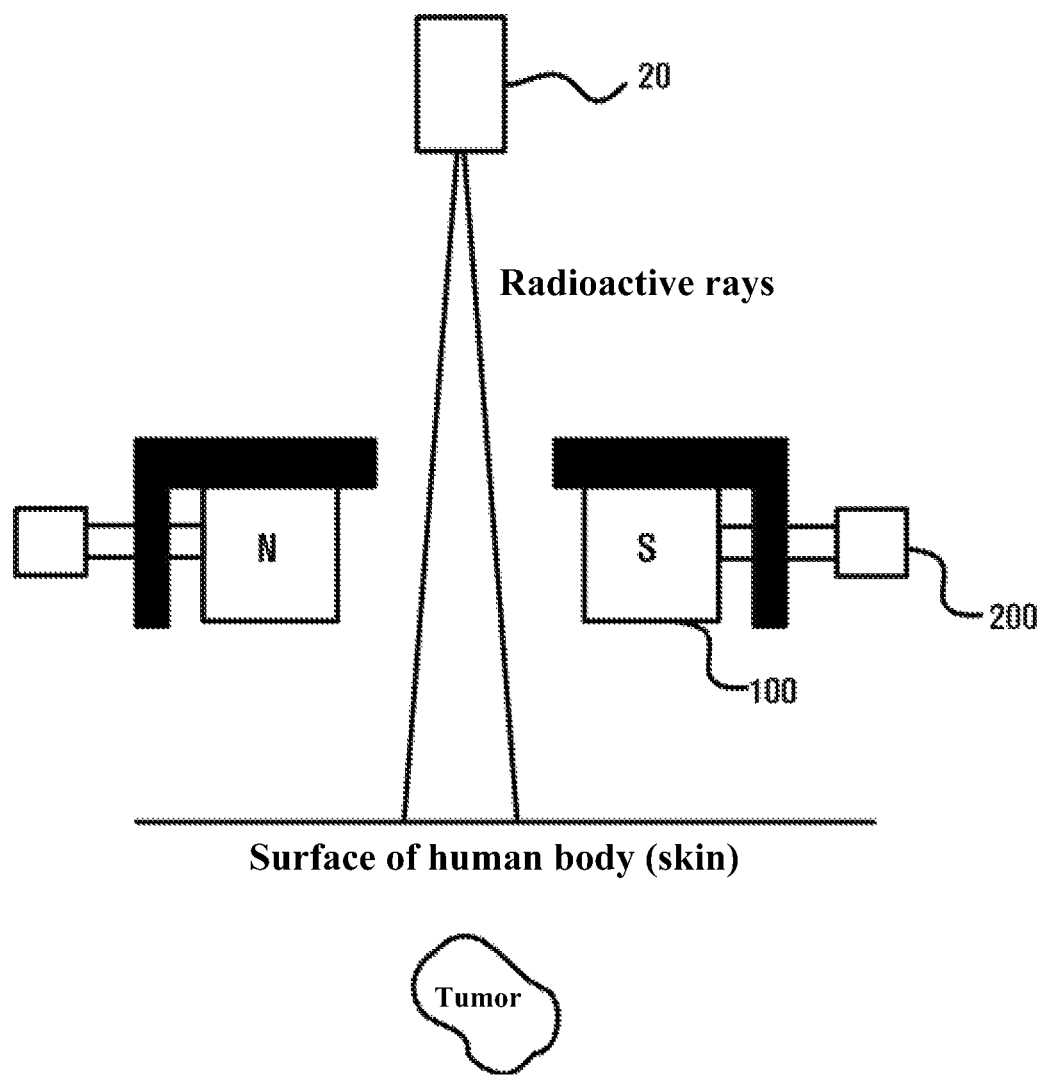
FIG. 5 is an exemplary view of a radiotherapy system including a magnetic field intensity adjusting unit that adjusts an intensity of a magnetic field by adjusting a distance between magnets of a magnetic field generator according to an embodiment of the inventive concept.

As an embodiment, when the magnetic field generator 100 includes a pair of magnets having opposite polarities, which are disposed on opposite sides on the movement route of a photon beam, the magnetic field intensity adjusting part 200 may have a structure for adjusting a spacing distance between the pair of magnets as illustrated in FIG. 5. The magnetic flux density increases while providing a strong magnetic intensity if the magnets of the opposite polarities are located close to each other, and the magnetic flux density decreases while providing a low magnetic intensity if the magnets of the opposite polarities are located far away from each other. Accordingly, the magnetic field intensity adjuster 200 may adjust the intensity of the magnetic field by adjusting a distance between the magnets having the opposite polarities, which are disposed out of field on incident radioactive ray.

For example, the magnets are movably disposed in a housing of the apparatus 10 for modulating build-up regions, and the magnetic field intensity adjuster 200 may be coupled to one of the magnets of the magnetic field generator 100 when passing through the housing in a screw manner. As the user turns the magnetic field intensity adjuster 200, the magnets in the housing moves so that the distance between the magnets may be adjusted.

Further, in another embodiment, when the magnetic field generator 100 includes electromagnets, the magnetic field intensity adjuster 200 may control the magnetic field generator 100 to form a magnetic field area.

Further, in another embodiment, a first distance adjusting unit is further included. The first distance adjusting unit functions to set a distance by which the magnetic field generator 100 is spaced apart from the surface of the skin of the target radiotherapy portion. That is, the first distance adjusting unit adjusts a distance (magnet-to-surface distance, MSD) between the magnetic field generator 100 (for example, the permanent magnets disposed on opposite sides) and the surface of the human body.

The first distance adjusting unit may set a location of the magnetic field generator 100 with reference to a surface of the human body. Further, in another embodiment, when the distance between the radioactive ray generator (for example, a photon beam output unit of the linear accelerator) and the surface of the human body is fixed, the first distance adjusting unit may set a distance (MSD) between the magnetic field generator 100 and the surface of the human body by setting the distance by which the magnetic field generator 100 is spaced apart from the magnetic field generator 100. For example, as will be described later, when the apparatus 10 for modulating a build-up region according to embodiments of the inventive concept is coupled to the radioactive ray output unit of the radiotherapy apparatus 20 in a module form, the first distance adjusting unit sets the distance (MSD) between the magnetic field generator 100 and the surface of the human body by adjusting the spacing distance from the radioactive ray output unit after the location of the radioactive ray output part from the surface of the skin is set.

Figure 6:
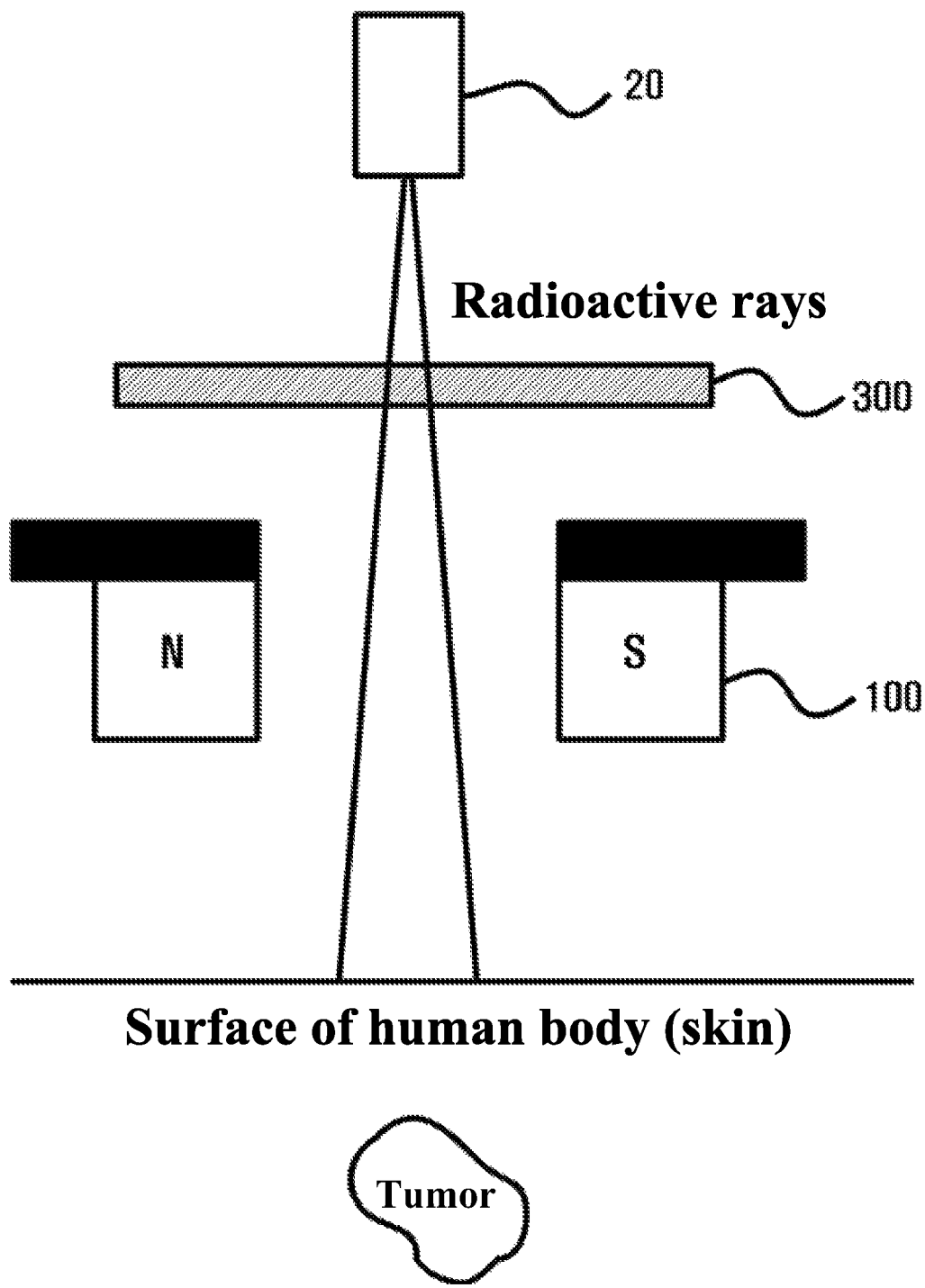
FIG. 6 is a diagram of a radiotherapy system including a beam spoiler according to an embodiment of the inventive concept.

Referring to FIG. 6, a radiotherapy system including the apparatus 10 for modulating build-up regions of a photon beam by using a magnetic field and a beam spoiler according to another embodiment of the inventive concept and including the magnetic field generator 100 and a beam spoiler 300.

The magnetic field generator 100 functions to disperse secondary electrons of a specific energy level or less by forming a transverse magnetic field on incident photon beams. In an embodiment, the magnetic field generator 100 includes a pair of electromagnets or permanent magnets that are disposed on opposite sides while having opposite polarities. That is, the magnetic field generator 100 functions to apply a magnetic field in a direction that is perpendicular to incident radioactive ray.

It is preferable that the radiotherapy apparatus 20 (or a radioactive ray generator) that uses the apparatus 10 for modulating a build-up region is a linear accelerator (LINAC) that generates a MV X-ray. The radiotherapy apparatus 20 delivers kinetic energy to secondary electrons through a reaction due to Compton effect on a surface of a material that is exposed to radiation due to the characteristics of X-ray beams in a generated MV area, and delivers the radioactive dose to the interior of the human body by using electrons.

The magnetic field generator 100 is disposed on the outside of the human body on a route along which a photon beam moves to a target portion (or a target portion). The magnetic field generator 100 generates a magnetic field in a direction that is perpendicular to the movement direction of the secondary electrons on the outside of the human body before the secondary electrons enter the interior of the human body, and the secondary electrons are biased or dispersed by a force of a magnetic field, for example, a Lorentz's force while passing through the magnetic field area formed by the magnetic field generator 100.

The beam spoiler 300 functions to generate secondary electrons as a photon beam passes through the beam spoiler 300. Because secondary electrons are generated by the Compton effect while the photon beam passes through the interior of the human body when radiotherapy is performed on the tumor located at a deep portion of the human body based on the photon beam, there exist secondary electrons that may provide a sufficient amount of radioactive rays to the target radiotherapy portion. However, when radiotherapy is performed on a tumor that is located at a portion that is close to a surface of skin instead of a deep portion of the human body, a sufficient amount of secondary electrons cannot be generated while the photon beam passes through the interior of the human body. Further, secondary electrons are generated in the linear accelerator itself that generates a photon beam and are provided together with a photon beam, but secondary electrons of a level, by which a radiotherapy effect is to be sufficiently provided to a tumor, cannot be provided.

Accordingly, in order to provide dose effect of a build-up region that is sufficient for a tumor tissue that is located at a specific depth from a surface of skin, the beam spoiler 300 that generates secondary electrons by the Compton effect due to a photon beam is disposed on a movement route for photons before a photon beam enters the interior of the human body.

A large amount of secondary electrons including secondary electrons having kinetic energy, by which the secondary electrons may reach a tumor tissue located in a specific depth from a surface of the skin, are generated while a photon beam generated by a radioactive ray generator (for example, a photon beam linear accelerator) of the radiotherapy apparatus 20 passes through the beam spoiler 300. Through this, the secondary electrons generated by the beam spoiler 300 together with the secondary electrons generated by the Compton effect while the photon beam passes provide a radiotherapy effect to the tumor tissue located at a specific depth from a surface of skin.

As an embodiment, the magnetic field generator 100 is disposed below the beam spoiler 300. That is, the magnetic field generator 100 is disposed such that, after a large amount of secondary electrons are generated in the beam spoiler 300 by the photon beam, a magnetic field is generated onto a route along which the secondary electrons move to the surface of the human body. Through this, the amount of radioactive rays in a tumor tissue located in a specific depth from the surface of the skin is increased, and the amount of radioactive rays in an area (that is, a normal tissue, particularly, the surface of the skin) located before the tumor tissue is deceased.

Figure 7:
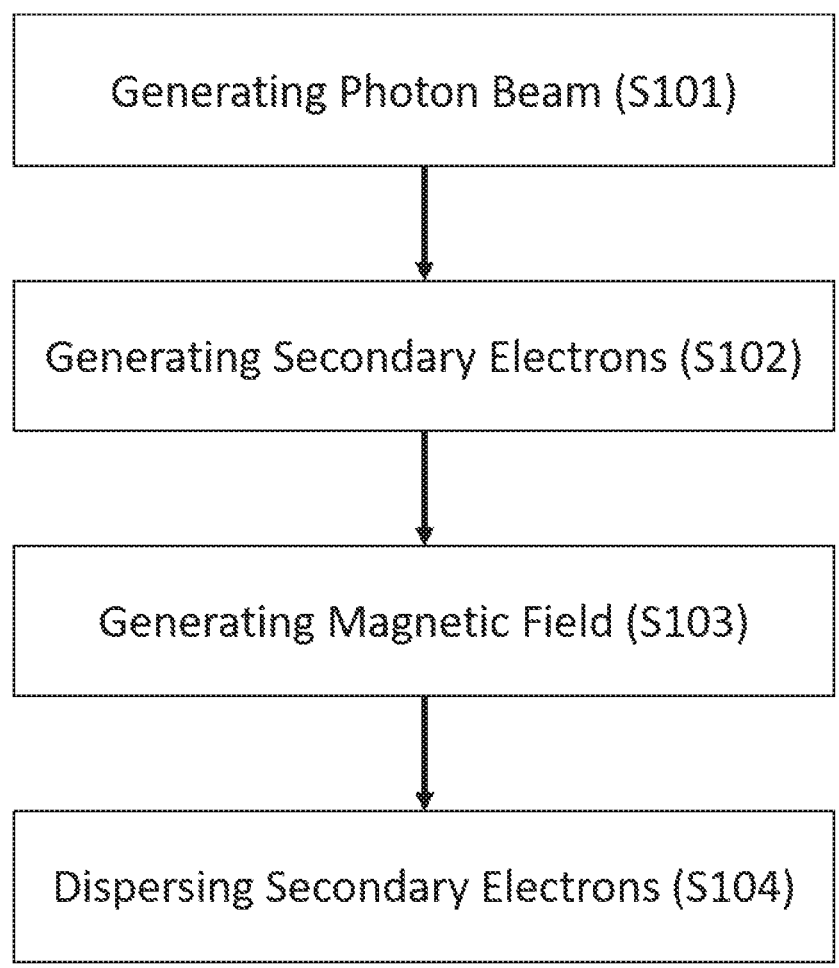
FIG. 7 is a flowchart of a radiotherapy method according to an embodiment of the inventive concept.

A process of modulating a depth dose provided to the body by the apparatus 10 for modulating a build-up region of a photon beam by using a magnetic field and a beam spoiler according to an embodiment of the inventive concept will be described. This process is also shown in FIG. 7. First, a large amount of secondary electrons are generated (S102) while a photon beam generated (S101) by the radiotherapy apparatus (that is, the linear accelerator) passes through the beam spoiler 300. The secondary electrons generated directly by the radiotherapy apparatus are present even before the photon beam enters the interior of the human body, but does not provide a dose that is sufficient enough to treat a tumor. Accordingly, the apparatus 10 for modulating a build-up region generates a large amount of secondary electrons while the photon beam passes through the beam spoiler disposed on the route of the photon beam outside the human body.

Thereafter, the magnetic field generator 100 generates a magnetic field (S103) and disperses the secondary electrons that influence the surface area of the skin due to the low kinetic energy of the secondary electrons (S104) by applying the generated magnetic field. If the kinetic energy of the secondary electrons is low, the secondary electrons fail to enter the depth of the skin and influence the surface of the skin. Because the secondary electrons are more greatly biased by a Lorentz's force as the kinetic energy of the secondary electrons is lower (that is, the movement speeds of the electrons are lower), the magnetic field generator 100 generates a magnetic field of a specific intensity in a direction that is perpendicular to the movement direction of the secondary electrons to eliminate the low-energy secondary electrons that influence the surface area of the skin. Through this, the low-energy secondary electrons are more biased and dispersed by the magnetic field and the high-energy secondary electrons (that is, the secondary electrons having high kinetic energy) travels towards the surface of the skin while being less biased.

Through this, the amount of the radioactive rays of the surface area of the skin decreases as the low-energy secondary electrons are eliminated, and a dose of the deep area from the surface of the skin is increased by the high-energy secondary electrons, which are not biased by a magnetic field, of the large amount of secondary electrons generated by the beam spoiler 300. A high dose of a desired level (for example, a depth dose in the case in which 6 MV is used, which is similar to the case of using a 4 MV photon beam) is provided only to a target radiotherapy area located in a specific depth from the surface of the skin, and a low dose, by which the skin is not damaged, is provided to the surface of the skin.

Further, in another embodiment, the magnetic field intensity adjuster 200 is further included. The magnetic field intensity adjuster 200 functions to adjust the intensity of a magnetic field of the magnetic field generator 100. Because the biasing degree of the secondary electrons varies according to the intensity of a magnetic field, the magnetic field intensity adjuster 200 sets a reference for kinetic energy of secondary electrons that fail to move towards the target radiotherapy portion and are biased and dispersed. For example, because secondary electrons having low kinetic energy reaches a tumor tissue to provide a radiotherapy effect when the target radiotherapy portion is located at a point that is close to the surface of skin as compared with the case in which the target radiotherapy portion is located at a deep point from a surface of skin, a reference for a level of kinetic energy of secondary electrons that is biased not to proceed towards the target radiotherapy portion may be set to be low by applying a magnetic field of a low intensity to the magnetic field generator 100.

When the magnetic field generator 100 includes a pair of magnets having different polarities which are disposed on opposite sides on the movement route of a photon beam, the magnetic field intensity adjusting part 200 may have a structure for adjusting a spacing distance between the pair of magnets as illustrated in FIG. 5. The magnetic flux density increases while providing a strong magnetic intensity if the magnets of the opposite polarities are located close to each other, and the magnetic flux density decreases while providing a low magnetic intensity if the magnets of the opposite polarities are located far away from each other. Accordingly, the magnetic field intensity adjuster 200 may adjust the intensity of the magnetic field applied to the secondary electrons by adjusting a distance between the magnets having the opposite polarities, which are disposed on opposite sides on the movement route of the radioactive ray.

For example, the magnets are movably disposed in a housing of the apparatus 10 for modulating a build-up region, and the magnetic field intensity adjuster 200 may be coupled to one of the magnets of the magnetic field generator 100 when the housing passes in a screw manner. As the user turns the magnetic field intensity adjuster 200, the magnets in the housing moves so that the distance between the magnets may be adjusted.

Further, for example, when the magnetic field generator 100 includes electromagnets, the magnetic field intensity adjuster 200 may control the magnetic field generator 100 to form a magnetic field area.

Further, in another embodiment, a first distance adjusting unit is further included. The first distance adjusting unit functions to set a distance by which the magnetic field generator 100 is spaced apart from the surface of the skin of the target radiotherapy portion. That is, the first distance adjusting unit adjusts a distance (magnet-to-surface distance, MSD) between the magnetic field generator 100 (for example, the permanent magnets disposed on opposite sides) and the surface of the human body.

The first distance adjusting unit may set a location of the magnetic field generator 100 with reference to a surface of the human body. Further, in another embodiment, when the distance between the radioactive ray generator (for example, a photon beam output unit of the linear accelerator) and the surface of the human body is fixed, the first distance adjusting unit may set a distance (MSD) between the magnetic field generator 100 and the surface of the human body by setting the distance by which the magnetic field generator 100 is spaced apart from the magnetic field generator 100. For example, as will be described later, when the apparatus 10 for modulating a build-up region according to embodiments of the inventive concept is coupled to the radioactive ray output unit of the radiotherapy apparatus 20 in a module form, the first distance adjusting unit sets the distance (MSD) between the magnetic field generator 100 and the surface of the human body by adjusting the spacing distance from the radioactive ray output unit.

Further, in another embodiment, a second distance adjusting unit that adjusts a distance between the beam spoiler 300 and the magnetic field generator 100 is further included. That is, the second distance adjusting unit adjusts a distance (a beam spoiler-to-magnet distance, BMD) between the beam spoiler 300 and the magnetic field generator 100.

Further, the beam spoiler 300 may be replaced in the apparatus 10 for modulating a build-up region. That is, the user may replace the beam spoiler 300 by a beam spoiler 300 of a different kind or a different thickness according to the treatment situation of the patient. That is, the user may minimize a dose of the volume portion to minimize a side-effect while providing a sufficient dose to the target radiotherapy portion, by adjusting a distance between a magnetic field and the beam spoiler or adjusting a thickness of the beam spoiler in comprehensive consideration of a depth, a volume, an adjacent distance, and the like of the radiotherapy portion of the patient.

Further, as in an embodiment, the apparatus 10 for modulating a build-up region may be manufactured of a module that is coupled to a radioactive ray output unit of the radiotherapy apparatus. That is, the apparatus 10 for modulating a build-up region is not disposed in the human body but may be coupled to the radiotherapy apparatus 20 to be used.

In detail, when radiotherapy has to be performed by using several radiotherapy apparatuses 20 (for example, linear accelerators), the apparatus 10 for modulating a build-up region according to the embodiments of the inventive concept may be coupled to the radiotherapy apparatuses 20 so that a plurality of apparatuses 10 for modulating a build-up region may not be disposed in a narrow surface area of the skin on the target radiotherapy portion. That is, a space around the patient is restricted so that it is difficult to install a magnetic field apparatus along the direction of a beam. Further, radioactive rays (for example, secondary electrons generated in the apparatus 10 for modulating a build-up region by a photon beam) by the radiotherapy apparatuses 20 may be easily individually controlled.

A radiotherapy apparatus based on a photon beam according to another embodiment of the inventive concept includes the apparatus 10 for modulating a build-up region according to the embodiments of the inventive concept, and a linear accelerator that outputs a photon beam of a specific intensity.

The linear accelerator (LINAC) functions to generate an MV X-ray, and the apparatus 10 for modulating a build-up region functions to provide a photon beam (that is, an MV X-ray).

As another embodiment, the apparatus 10 for modulating a build-up region is electronically connected to the radiotherapy apparatus 20 to adjust at least one of an intensity of a magnetic field of the magnetic field generator 100 (for example, a distance between magnets or an intensity of electromagnets itself), a spacing distance (magnet-to-surface distance, MSD) between the magnetic field generator 100 and a surface of the skin, and a spacing distance (beam spoiler-to-magnet distance, BMD) between the beam spoiler 300 and the magnetic field generator 100, based on a radiotherapy condition (for example, a depth of a tumor from a surface of skin). To achieve this, the apparatus 10 for modulating a build-up region may further include a controller that performs a control based on a signal delivered from the linear accelerator.

The inventive concept has the following effects.

First, when a radioactive ray is irradiated to a tumor portion of the patient, a degree, by which a normal tissue located on a route along which the radioactive ray moves to the tumor portion is damaged, may be reduced. As the low-energy secondary electrons that fail to reach the tumor tissue are eliminated in advance, the number of the secondary electrons that influence a normal tissue located before a tumor tissue on a movement route of a radioactive ray is reduced while an increased dose is provided to the tumor tissue. That is, a damage to a surface of skin by a radioactive ray may be prevented by increasing a depth by which the dose is increased by the secondary electrons. Second, a dose may be sufficiently provided to a tumor tissue located in a specific depth from a surface of a human body portion by high-energy electrons provided by the beam spoiler through the inventive concept. In particular, among secondary electrons generated by the beam spoiler, the secondary electrons having energy of a reference level or less (that is, which do not have energy by which they may reach a tumor tissue) may be dispersed by a magnetic field so that a dose may be decreased in a normal tissue (for example, a surface of skin) located before a tumor tissue while a dose is increased in a tumor tissue at a target radiotherapy point.

Further, an amount of radioactive rays that show a radiotherapy effect at a target radiotherapy point at which a tumor is located when a zone in which a photon beam passes through the interior of the human body is not long (for example, when a tumor is very close to or adjacent to skin and a volume of the target is not large) may be increased. In particular, the apparatus for modulating a build-up region may be easily installed outside the human body to be easily applied to radiotherapy of a skin cancer or a Gottic cancer, a tumor of which is located adjacent to skin.

Further, instead of locally applying a strong magnetic field to only the interior of the human body, by applying a magnetic field from the outside of the human body before a radioactive ray enters into the interior of the human body, a strong magnetic field is not applied to the interior of the human body so that a clinical application may be possible. Further, because a magnetic field provides secondary electrons on the outside of the human body, a control of the secondary electrons by the magnetic field may be easily achieved.

Further, the directions of the magnetic field may be diversified for modulation of a dose by using beams of various directions for radiotherapy. Because individual magnetic fields are applied from the outside of the human body according to directions of beams when radiotherapy is performed by using the plurality of linear accelerators, magnetic fields that agree with the conditions of the linear accelerators may be applied such that the linear accelerators may provide a dose build-up effect to the interior of skin and provide a low dose to the surface of the skin (that is, provide an amount of radioactive rays that is similar to the amount of radioactive rays when the radioactive rays are provided as an open beam while a small amount of radioactive rays are provided as compared with the case in which a tissue equivalent material is attached). Through this, dose effect of a build-up region may be accurately provided to a tumor tissue by using the plurality of linear accelerators.

When a radioactive ray is irradiated to a tumor portion of the patient, a degree, by which a normal tissue located on a route along which the radioactive ray moves to the tumor portion is damaged, may be reduced. As the low-energy secondary electrons that fail to reach the tumor tissue are eliminated in advance, the number of the secondary electrons that influence a normal tissue located before a tumor tissue on a movement route of a radioactive ray is reduced.

Further, a dose may be sufficiently provided to a tumor tissue located in a specific depth from a surface of a human body portion by high-energy electrons provided by the beam spoiler through the inventive concept. In particular, among secondary electrons generated by the beam spoiler, the secondary electrons having energy of a reference level or less (that is, which do not have energy by which they may reach a tumor tissue) may be dispersed by a magnetic field so that a dose may be decreased in a normal tissue (for example, a surface of skin) located before a tumor tissue while a dose is increased in a tumor tissue at a target radiotherapy point.

Although the exemplary embodiments of the inventive concept have been described with reference to the accompanying drawings, it will be understood by those skilled in the art to which the inventive concept pertains that the inventive concept can be carried out in other detailed forms without changing the technical spirits and essential features thereof. Therefore, the above-described embodiments are exemplary in all aspects, and should be construed not to be restrictive.

What is claimed is:

1. A radiotherapy assistant apparatus for modulating a build-up region of a photon beam for a radiotherapy, the apparatus comprising:
    a magnetic field generator that generates a magnetic field that has a direction perpendicular to a movement direction of the photon beam, the magnetic field generator is disposed on a movement route along which the photon beam moves toward a target portion of the radiotherapy; and
    a magnetic field intensity adjuster that adjusts an intensity of the magnetic field generated by the magnetic field generator,
    wherein the magnetic field generator disperses secondary electrons that have particular energy levels equal to or lower than a preset value.

2. The apparatus of claim 1, wherein
    the magnetic field generator comprises a pair of magnets having opposite polarities,
    the magnets are disposed on opposite sides on the movement route, and
    the magnetic field intensity adjuster adjusts a spacing distance between the magnets.

3. The apparatus of claim 2, further comprises:
    a housing containing at least a part of the magnetic field generator and at least a part of the magnetic field intensity adjuster, wherein
    the magnetic field intensity adjuster is coupled to one of the magnets of the magnetic field generator and passes through a wall of the housing in a screw manner.

4. The apparatus of claim 1, further comprising:
    a first distance adjuster that adjusts a distance between the magnetic field generator and a surface of skin on the target portion of the radiotherapy.

5. A radiotherapy system for a radiotherapy, the system comprising:
    a radiotherapy apparatus comprising a radioactive ray output that outputs radioactive rays; and
    a radiotherapy assistant apparatus according to claim 1, wherein
    the radiotherapy assistant apparatus is coupled to the radioactive ray output of the radiotherapy apparatus.

6. The system of claim 5, wherein the radiotherapy assistant apparatus is electronically connected to the radiotherapy apparatus and adjusts at least one of the intensity of the magnetic field generated by the magnetic field generator and a distance between the magnetic field generator and a surface of skin on the target portion of the radiotherapy, based on a radiotherapy condition.

7. The system of claim 6, wherein the radiotherapy assistant apparatus further comprising:
    a controller that performs a control based on a signal received from the radiotherapy apparatus.

8. The system of claim 5, wherein the radioactive ray output of the radiotherapy apparatus comprises a linear accelerator that outputs the photon beam of a particular intensity.

9. A radiotherapy assistant apparatus for modulating a build-up region of a photon beam for a radiotherapy, the apparatus comprising:
    a magnetic field generator that generates a magnetic field that has a direction perpendicular to a movement direction of the photon beam, the magnetic field generator is disposed on a movement route along which the photon beam moves toward a target portion of the radiotherapy; and a beam spoiler disposed on the movement route, the beam spoiler generates, when the photon beam passes through the beam spoiler, secondary electrons, wherein the magnetic field generator disperses secondary electrons having particular energy levels equal to or lower than a preset value, among the secondary electrons generated by the beam spoiler and secondary electrons included in the photon beam.

10. The apparatus of claim 9, further comprising:

a magnetic field intensity adjuster that adjusts an intensity of the magnetic field generated by the magnetic field generator.

11. The apparatus of claim 10, wherein the magnetic field generator comprises a pair of magnets having opposite polarities, the magnets are disposed on opposite sides on the movement route, and the magnetic field intensity adjuster adjusts a spacing distance between the magnets.

12. The apparatus of claim 11, further comprises:

a housing containing at least a part of the magnetic field generator and at least a part of the magnetic field intensity adjuster, the magnetic field intensity adjuster is coupled to one of the magnets of the magnetic field generator and passes through a wall of the housing in a screw manner.

13. The apparatus of claim 9, further comprising:

a first distance adjuster that adjusts a distance between the magnetic field generator and a surface of skin on the target portion of the radiotherapy.

14. The apparatus of claim 9, wherein the magnetic field generator is disposed below the beam spoiler.

15. The apparatus of claim 14, further comprising:

a second distance adjuster that adjusts a distance between the beam spoiler and the magnetic field generator.

16. A radiotherapy system for a radiotherapy, the system comprising:

a radiotherapy apparatus comprising a radioactive ray output that outputs radioactive rays; and a radiotherapy assistant apparatus according to claim 9, wherein the radiotherapy assistant apparatus is coupled to the radioactive ray output of the radiotherapy apparatus.

17. The system of claim 16, wherein the radiotherapy assistant apparatus:

is electronically connected to the radiotherapy apparatus, and adjusts at least one of an intensity of the magnetic field generated by the magnetic field generator, a distance between the magnetic field generator and a surface of skin on the target portion of the radiotherapy, and a distance between the beam spoiler and the magnetic field generator, based on a radiotherapy condition.

18. The system of claim 17, wherein the radiotherapy assistant apparatus further comprising:

a controller that performs a control based on a signal received from the radiotherapy apparatus.

19. The system of claim 16, wherein the radioactive ray output of the radiotherapy apparatus comprises a linear accelerator that outputs the photon beam of a particular intensity.

20. A radiotherapy method for modulating a build-up region of a photon beam for a radiotherapy, the method comprising:

generating, by a linear accelerator of a radiotherapy apparatus, the photon beam;

generating, by a beam spoiler of a radiotherapy assistant apparatus, secondary electrons when the generated photon beam passes through the beam spoiler;

generating, by a magnetic field generator of the radiotherapy assistant apparatus, a magnetic field that has a direction perpendicular to a movement direction of the photon beam; and dispersing, by the magnetic field generator of the radiotherapy assistant apparatus, secondary electrons having particular energy levels equal to or lower than a preset value, among the secondary electrons generated by the beam spoiler and secondary electrons included in the photon beam, wherein an intensity of the magnetic field generated by the magnetic field generator is adjusted by a magnetic field intensity adjuster of the radiotherapy assistant apparatus, based on a radiotherapy condition.

* * * * *